(12) United States Patent
Owen et al.

(10) Patent No.: US 7,078,378 B1
(45) Date of Patent: Jul. 18, 2006

(54) METHOD OF TISSUE REPAIR II

(75) Inventors: Earl R. Owen, Lane Cove (AU); Peter Maitz, Lane Cove (AU); Rodney I. Trickett, North Rocks (AU); Judith M. Dawes, Epping (AU); James A. Piper, Pennant Hills (AU); Peter Dekker, Elanora (AU)

(73) Assignee: Avastra Ltd., Sydney (AU)

( * ) Notice: Subject to any disclaimer, the term of this patent is extended or adjusted under 35 U.S.C. 154(b) by 0 days.

(21) Appl. No.: 09/719,889

(22) PCT Filed: Jun. 18, 1999

(86) PCT No.: PCT/AU99/00495

§ 371 (c)(1),
(2), (4) Date: Feb. 21, 2001

(87) PCT Pub. No.: WO99/65536

PCT Pub. Date: Dec. 23, 1999

(30) Foreign Application Priority Data

Jun. 18, 1998 (AU) ...................................... PP4214

(51) Int. Cl.
*A61K 38/00* (2006.01)

(52) U.S. Cl. ............................ 514/2; 514/21; 514/773; 514/776; 530/362

(58) Field of Classification Search ................ 530/350, 530/362; 514/12, 21, 773, 776; 106/124.1; 606/2, 8, 213, 214
See application file for complete search history.

(56) References Cited

U.S. PATENT DOCUMENTS 5,156,613 A * 10/1992 Sawyer
5,713,891 A * 2/1998 Poppas
5,749,895 A * 5/1998 Sawyer et al.
6,323,037 B1 * 11/2001 Lauto et al. .................. 436/86

FOREIGN PATENT DOCUMENTS

WO      WO 96/22054      7/1996

* cited by examiner

*Primary Examiner*—Bruce R. Campell
*Assistant Examiner*—B. Dell Chism
(74) *Attorney, Agent, or Firm*—Morrison & Foerster LLP

(57) ABSTRACT

A substantially solid biomolecular solder for joining tissue comprising a partially denatured biomolecule. The solder can be formed into shapes to suit the needs of a user. The invention also relates to methods for joining tissue and methods for preparing the solder.

91 Claims, 12 Drawing Sheets

Blood flow

Blood flow

Blood Flow →

METHOD OF TISSUE REPAIR II

CROSS-REFERENCE TO RELATED APPLICATIONS

This application, filed under 35 U.S.C. 371, claims the benefit of priority to international application PCT/AU99/00495, filed Jun. 18, 1999, which was published under PCT Article 21(2) in English, and is hereby incorporated by reference.

TECHNICAL FIELD

The present invention relates to methods for joining: living tubular tissues; organs and their coverings; skin and appendages; as well as the various internal and peripheral nerves of the body, the spinal cord and its ramifications. The invention also relates to a solder for use in those methods and methods for preparing the solder.

BACKGROUND ART

In repairing living tissues, sutures or clips are routinely used to close defects, join planes of tissues or to join bodily tubes together (anastomoses).

This involves the placing of materials in the body which cause some damage to the tissues involved, but hold those tissues in apposition while the body's own healing processes effect a more permanent join. The damage that various joining materials cause varies but even careful placement of microsutures in the smallest of bodily tubes during an anastomosis produces a fibrous tissue reaction around each of the suture materials left in situ.

Joins, however made, take time, and those joins made by placing individual sutures in tubular joins are the most time consuming. Sewing in a ring of sutures to effect such a join inside the body may demand a large incision to obtain the access required to effect enough surgical freedom to manipulate the equipment and instruments required. Microsuturing requires considerable skill.

Arteries and Other Tubes

Fluids, and materials suspended within them, can travel along the body's patent tubes. Arteries carry blood from the heart to other organs and tissues in the body. They have 3 layers, an inner specialised mucosa (termed the intima), a thicker, middle, muscular and structural layer which contains collagen and elastin connective proteins (the media), and an outside layer which is a scaffold with fibrous tissue, blood vessels and nerves all supplying the functions of the artery (the adventitia). The inner volume of the artery is the lumen.

For tubes such as arteries to function in transporting blood at high pressure, they need to be strong. They are actually active in transporting a pressure wave of blood by expanding and relaxing (systole and diastole) as the bolus of blood passes. Joining such active tubes requires such physiological activity as promoting blood flow to be considered and the design of methods of anastomosis that will allow the activity to continue after the join.

Injuries to an artery are potentially very serious for an animal or human, as blood flowing through the artery is at high pressure and blood loss can be rapid. If the intima layer is damaged, then the middle, structural layer, the media, is exposed to blood. This triggers an important repair mechanism which acts to seal the wound and prevent further bleeding by the formation of blood clots on the wound, caused by blood coming into contact with the exposed collagen of the media.

Although microsuturing is the standard clinical repair technique for a severed artery, it has several disadvantages. A high skill level is required to make between 6 and 12 separate sutures to repair the artery. The sutures remain in the body acting as a site for fibrous tissue to form due to foreign body reaction, and this fibrous tissue is a point of weakness in the artery even after it is deemed to have healed. Although suturing does not produce a fluid-tight seal, surgeons usually rely on blood clotting triggered by the mechanism described above to seal the vessel soon after the repair is complete.

A number of laser-assisted welding techniques have been explored in order to find a more convenient technique which does not lead to so much scarring. These almost always need stay sutures (sutures used to join the vessels before laser treatment, which may or may not be removed subsequently) for a successful outcome. In this case the two vessel ends are held together to allow stay sutures to be inserted and then a laser is used to heat the tissue at the join so that proteins at the site are coagulated and bond together. Lasers such as the infra-red holmium-doped YAG and carbon dioxide lasers have been used because these produce wavelengths which are strongly absorbed by water in the tissue. Alternatively a dye solution may be applied to the tissue to enhance light absorption at a suitable laser wavelength. In any case, it is crucial that the intima layers of the 2 ends are in continuity, to avoid a blockage or a clot and to promote smooth laminar flow in the repaired vessel. This is difficult to achieve in thick-walled vessels where the laser energy may not be absorbed through all three layers of the vessel to form a strong weld with a smooth intima layer.

Some protein glues have been used to repair blood vessels, such as fibrin (which triggers a blood clotting reaction to effect a tissue join). A possible disadvantage of such a glue is the potential to be associated with blood clotting within the vessel, partially or wholly obstructing it.

Laser-activated fluid albumin solder has also been used, but the solder has required stay sutures to achieve sufficient repair strength for arteries which carry blood at high pressure. Fluid glues and solders tend to run between the tissue ends, risking blockage of the inner lumen, and are difficult to control and position accurately on the tissue repair. To attain a seal, they have been applied circumferentially around the join, which is then circumferentially welded. These joins later show thick scarring which can cause stricture or blockage of the vessel or tube.

There is also a lack of precision in such techniques, because of differences in the glue or fluid solder consistency, variations in the type of applicator device used to apply the glue or fluid solder, and the pressure needed to form a join.

A major drawback with current fluid solders is that they rapidly deteriorate and change composition when introduced into moist environments.

Similarly, existing solid solders must be kept dry when introduced to moist arteries, to prevent them from absorbing moisture, weakening their internal bonding and losing strength, even though this occurs more slowly than for fluid solders.

The repair of other bodily tubes is similar in is concept. Since the structure of each tube is specialised to its function and the nature of its contents there must be careful choice of the method of tube repair so that it will not interfere with the tube function, and in particular with maintaining the inner lumen of the tube.

Peripheral Nerves

The electrical signals that control the body's organs and transmit information back and forth to the central nervous system (CNS) travel along peripheral nerves.

A peripheral nerve has an outer membrane consisting of connective tissue such as collagen. This membrane (epineurium) protects and holds separate bundles of nerves or fascicles together. The fascicles group together nerve axons supplying a specific region of the body and are bounded by perineurium membranes. Each axon is supported by a Schwann cell within the fascicle. Nerve metabolism is sustained by the vascular system from both outside and within the nerve.

When a peripheral nerve is cut all axons distal (further from the spine) to the wound change their properties. Even when the nerve is reconnected, these axons continue to degenerate distally. The Schwann cells which normally wrap themselves around the axons as insulation, guide regenerating axons. Joining nerves as accurately as possible by lining up corresponding fascicles enables the enclosed axons to more efficiently regenerate.

Peripheral nerves can have diameters ranging from approximately 1 cm to approximately 50 micrometers.

Operating on nerves and other tissues of small dimensions has been facilitated by using magnification and special microsurgical equipment. Accurate nerve repairs need to be effected at the fascicular level ensuring that regeneration is along the correct bundle leading to the original area those axons supplied.

The current technique of peripheral nerve repair uses microsuturing. This technique requires a dedicated trained surgeon as microsuturing of just one of the many fascicles with three or more microsutures (using say a 70 micron diameter needle and 30 micron thread) can take very long operating times. There is the prospect of added damage to the inner axons due to sutures penetrating the thin perineurial sheath. The use of sutures results in some scarring of the repair due to foreign body reaction. Excessive scarring impairs nerve function and may be associated with painful neuromas. There is also evidence that in the long term, scar tissue formation and scar maturation can impair the joined nerve.

Work has been performed on the use of lasers alone in effecting nerve joins. To date the welds have typically been made using infrared lasers such as carbon dioxide lasers which rely on water absorption for energy-transfer. Tissue preparation before welding relies on overlapping the nerve membranes. One of the problems of laser welding has been the fact that the intact axonal tissue is under pressure within the fascicle, so that when it is cut the axons extrude. Laser treatment can thus lead to denaturation of the axon material leading to scarring and proliferation of fibrous tissue.

Laser-activated protein solders have also been tried, as described for the artery and blood vessel case above. Again because of difficulties in controlling fluid solders, and the weakness of the resulting bonds in a moist environment, these repairs are usually too weak without the addition of stay sutures. This complicates the surgical technique and leads to additional scarring and foreign body reaction.

The bonds formed to date as described in the prior art using laser welding have typically lacked strength and thus microsuturing has been used in addition to welding to strengthen these joins.

Solutions to at least some of these problems are taught in WO96/22054. The present invention relates to alternative solutions.

DESCRIPTION OF THE INVENTION

In a first aspect the present invention provides a biomolecular solder comprising an at least substantially solid composition of at least one biomolecule which has been mixed at high concentration with an aqueous solvent, which composition is created to at least partially denature the biomolecular components of the solder and to at least partly dry the solder.

The biomolecule(s) is typically proteinaceous but it is envisaged that other naturally occurring biomolecules could be used as alternatives. Further, analogues of biological, biodegradable polypeptides could be used. Analogues of biological, biodegradable polypeptides useful in the solders of the invention include synthetic polypeptides and other molecules capable of forming the solder of the invention but which do not cause adverse reaction in the tissue undergoing repair.

Where the biomolecule is a protein, the protein can be any protein or mixture of proteins but is preferably bio-degradable in the relevant host. Examples of suitable proteins include albumins, collagen, fibrinogen and elastin. Suitable proteins are typically those which can be cross-linked to form a matrix and which can be resorbed by the body. Where combinations of proteins are used it is envisaged that those combinations will be of proteins having similar denaturation temperatures. An example is the combination of albumin and collagen. Use of different albumins is contemplated including bovine, horse, human, rat, ovine and rabbit albumin. The choice of a particular albumin may be made to reduce immunological reaction in the patient to the solder. It is envisaged that there will be circumstances where the albumin used may be chosen to match the patient's blood type and possibly even more specifically with regard to histocompatibility markers of the patient in question.

The solvent is typically water but other aqueous solvents including saline may be used provided that any salt etc present does not adversely affect the solder upon denaturation.

The solder can be formed from a protein paste made up of highly concentrated protein in an aqueous solvent which is typically water. Highly concentrated protein encompasses protein concentrations in the range of 40 to 80% w/w. Preferably the protein concentration is in the range of 45 to 75% w/w. More preferably, the protein concentration is in the range of 50 to 60% w/w. The range of 50 to 60% is especially preferred for bovine serum albumin, or rat or rabbit or ovine or human albumin. The starting concentration of protein loses water (or aqueous solvent) as it dries or is dried during processing. The prepared solder may contain little or no solvent.

It is preferred to incorporate light-absorbing material, such as a dye, into the solder, to improve energy deposition in the solder. An example of a suitable dye is indocyanine green which is preferably incorporated at a concentration within the range 0.1 to 2.5% w/w. Other suitable dyes include methylene blue and fluorescein isothiocyanate. It will be understood that the light-absorbing material is chosen to be appropriate to the energy source that is used in forming tissue repairs involving the use of the solder. The light absorbing substance may be incorporated by being added to the solvent and dissolved in it prior to addition of the biomolecule(s) to the solvent.

In one embodiment the solder is prepared from a composition of:

55–75% w/w albumin

45–25% w/w water 0.25% w/w indocyanine green

The albumin may be bovine, rabbit, human, ovine or rat albumin.

The at least partial denaturation of the biomolecule(s) substantially reduces the solubility of the solder. Typically the biomolecule(s) of the solder is denatured to a sufficient extent to ensure that the solder will have sufficient longevity in vivo for the repair, for which the solder is being used, to be formed. Denaturation favourably alters the mechanical properties of the solder so that on moistening it exhibits similar mechanical properties to the tissue under repair. The denaturation can be effected by heat, light, radiation, ultrasound or chemical means. Typically the heat denaturation is carried out in an aqueous environment such as in a water bath in steam or in pressurised steam. Without wishing to be bound by theory, the present inventors believe that the aqueous environment permits at least partial denaturation without dissolution and with the maintenance of "structural" water involved in the integrity of the biomolecule(s). Denaturation may be effected before, during or after shaping of the solder.

The solder can be provided in a variety of shapes. In particular, the solder of the invention is suitable for extruding into tubular forms, a form that cannot readily be achieved with prior art solders. It can also be extruded into a partial tube which has a curved cross section with an elongate open channel which can be wide or narrow. The solder can be prepared with a smooth surface or with a surface that is at least slightly roughened. Roughening may be of assistance in enhancing contact between tissue and solder. The roughening may provide a profile which appears smooth at macroscopic level but rough at microscopic level. The tubular and partially is tubular forms typically have a round or ovoid profile but other profiles are also contemplated including square crenulated and other geometric forms. The tubular solder of the invention can be tapered or of uniform cross section. The tubular solder of the invention is well suited to nerve repair applications and is particularly well suited to vascular applications in which the moisture content makes prior art solders unsuitable. The solder can be prepared in other shapes as required for particular applications including strips, patches, solid rods and hollow cubes with at least one flanged end.

Various adjuvants can be added to the solder to promote rapid or more complete tissue healing, eg fibrinogen (for blood vessels), growth factors, sodium hyaluronate (for improved viscous handling and possibly better healing), hormones, and/or anticoagulants, such as heparin.

Various fibrous materials can be added to the solder to improve the strength of the solder [eg collagen or polytetrafluoroethylene fibre (which is sold under the brand names goretex and teflon) or ceramic fibres]. The fibres are typically biocompatible polymers. The denaturation of the solder with fibrous materials within it may be by chemical means (such as with acid or hydroxide) or by heat and could include bonding of the protein to the fibres.

The solder need not be of uniform composition throughout. In some applications it will be desirable to include one or more adjuvants in one or more parts of the solder and not in others. Similarly, it may be desirable to incorporate fibres in some parts and not others or else different fibres in different parts. Further, one or more light-absorbing substances may be incorporated in some parts of the solder and not others or the light-absorbing substance may be incorporated at different concentrations throughout one or more parts of the solder. It will be recognised that such variations may be particularly useful with various shaped forms of the solder such as tubes. Still further, different parts of the solder may be denatured to different extents and different parts of the solder may be provided with different surface textures, such as being smooth in some parts and at least slightly roughened in other parts.

The solder can be applied to a mesh, stiffener or graft material made from, for instance, a metal, synthetic fibre or plastic. Because of its pliability, the solder may be embedded into spaces in the mesh or it may be applied as a covering to all or part of the mesh, stiffener or graft material. In one embodiment, it may be applied only to the ends of a graft material, mesh or stiffener to effect welding of the graft material, mesh or stiffener to the appropriate tissue.

The formation of such materials may involve coextrusion or coating of a biologically inert porous structure (such as a goretex tube or shape) with solder. Where a coating is utilised in this embodiment, the solder may be initially formulated in a fluid form, that is, with a substantially lower concentration of the biomolecule(s). The fluid solution is applied, allowed to dry and may be reapplied and allowed to dry before being at least partially denatured. The drying process reduces the solvent content so that the final consistency of the solder is the same as that achieved by forming the solder from the high concentration solution as described above.

The solder of the invention can be introduced to the relevant tissue by the surgeon, and placed in the correct position, using forceps. If necessary, the solder can be cut to a required size or shape during surgery.

The at least partially denatured biomolecule(s) of the solder has strong internal bonding and is substantially unaffected by water absorption. Any water absorption that occurs acts to enhance the flexibility of the solder rather than causing its dissolution or disruption.

The solder can be introduced into the relevant tissue in an appropriately moistened form. In this form the solder is flexible and will not fracture when cut, squeezed or manipulated with surgical instruments.

The solder can be sterilised after denaturing and before use, by for instance gamma ray irradiation, for instance at 2000 rad/min for 50 minutes. Other suitable forms of sterilisation include autoclaving, steam treatment and heat treatment.

Activation of tissue bonding by the solder is induced by heat. This can be achieved in a variety of ways but laser activation is the most common. Because the biomolecule(s) is already at least partially denatured, dissolution is at least substantially prevented, allowing time for more complex manipulations to be completed. Laser activation of bonding through overlying tissue is possible with this solder, that is, the solder can be applied under, over, or under and over the tissue to be joined.

In a second aspect the present invention provides kits of solder tubes, partial cubes and shapes formed from solder of the first aspect of the invention. The kits may comprise tubes, partial tubes and/or shapes of different sizes to suit different surgical applications. The different sized tubes can include different lumen sizes, wall thicknesses and lengths. It is envisaged that tubes will often be cut to length to suit the repair to be effected during surgery thus minimising the number of different lengths that need to be provided. The kits can include tubes, partial tubes or shapes fashioned from solders made with different biomolecules, including those made with biomolecules which reflect the need to match the repair material for histocompatibility markers in the animal or human patient in which the repair is to be made. Further the tubes, partial tubes or shapes can be provided in different versions including a series of different adjuvants, light-absorbing substances and/or fibres as well as with different solder compositions throughout the tubes, partial tubes or shapes.

In a third aspect the present intention provides a method of preparing a solder of the first aspect, the method comprising the steps of forming a high concentration solution of one or more biomolecule(s) in an aqueous solvent, at least partially denaturing the biomolecule(s) and drying the solder.

Typically the method includes forming the solid solder into a shape which is preferably a hollow tube. Other suitable shapes include partial tubes, strips, patches, hollow tubes with at least one flanged end or solid rods suitable for the tissue being repaired.

To form hollow tubes, the solder can be extruded into hollow tubes by the use of a high pressure extrusion and die set, manufactured of stainless steel or other suitable biologically inert material, which may have very smooth surfaces to permit smooth solder shapes to be extruded. Shaped solders can also be prepared by injection moulding. Alternatively, the extruded solder may be prepared with an at least slightly roughened surface to enhance contact between the solder and the tissue to which it is applied. In this form, the solder may have a surface which is roughened on a microscopic scale but appears smooth on a macroscopic scale. The tube dimensions can be in the range of 0.2 mm to 6 cm in diameter, with variable wall thickness, which depending on the cube diameter and strength of the solder, can be as low as 50 µm. It will be understood that for veterinary applications, where very large animals and very small animals may be involved that even greater diversity of tube sizes may be required to suit the needs of various physiological tubes in need of repair. The solder of the intention is suited to the precision manufacture of tubes of desired dimensions.

In one embodiment, the method for forming a tubular solder comprises forming a high concentration solution of at least one biomolecule in an aqueous solvent, extruding the solution without permitting it to dry, allowing the extruded material to dry, at least partially denaturing the extruded material, allowing the at least partially denatured, extruded material to dry, moistening the material, cutting the material to length, finally drying the material and sterilising the material.

The starting concentration of biomolecule loses aqueous solvent as it dries or is dried during processing. In the prepared solder, little or no solvent may be present.

The method may include incorporating a light-absorbing material, such as a dye, into the solder, to improve light energy deposition in the solder, with the light-absorbing material being chosen to be appropriate to the energy source that is used in forming tissue repairs involving the use of the solder. Where a light-absorbing material is incorporated this may be achieved by mixing the light absorbing substance into the solvent and then adding this solution to the biomolecule(s) for mixing.

Indocyanine green dye (for example, prepared at a concentration of 0.25 mg/ml where the solder is placed over the tissue to be joined and 2.5 mg/ml where the solder is placed under the tissue to be joined) can be incorporated into albumin protein paste (approximate concentration on mixing 60% weight/weight) which is then preferably denatured by the immersion of the protein solder in a water bath at elevated temperature (preferably around 85° C.) for a suitable period of time (preferably 30 seconds) or in steam where temperatures over 10° ° C. are used.

Typically the biomolecule(s) of the solder is denatured to a sufficient extent to ensure that the solder will have sufficient longevity in vivo for the repair for which the solder is being used to be formed. The denaturation can be effected by physical leans such as beat (direct or indirect), light, radiation or ultrasound or chemical means. Typically the denaturation is carried out in an aqueous environment such as a water bath in steam or in pressurised steam. This can be achieved where the biomolecule(s) is proteinaceous by immersing the protein paste in hot liquid (preferably water) at a temperature of over 40° C. (preferably 85° C. for bovine se albumin (BSA)) for a suitable time (preferably 30 seconds for (BSA) or in steam where temperatures over 100° C. are used, for a suitable period of time. For human or rabbit serum albumin, steam treatment by for instance autoclaving at temperatures between 100° C. and 150° C. are preferred, with temperatures between 110° C. and 130° C. being more preferred example of a suitable temperature is about 120° C. The steam treatment is typically for about 10 minutes. Denaturation may be effected before, during or after shaping of the solder.

The method can include the addition of various adjuvants to the solder, eg fibrinogen (for blood vessels), growth factors, sodium hyaluronate (for improved viscous handling and better healing), hormones, and/or anticoagulants, such as heparin.

The method can also include the incorporation of various fibrous materials into the solder co improve the strength of the solder [eg collagen or polytetrafluoroethylene fibre, or ceramic fibres]. The fibres are typically biocompatible polymers. The denaturation of the solder with fibrous materials within it may be by chemical means (such as with acid or hydroxide) or by heat and could include bonding of the biomolecule(s) to the fibres.

The method may be modified to produce a solder that is not of uniform composition throughout. For instance, in some applications it will be desirable to include one or more adjuvants in one or more parts of the solder and not in others. Similarly, it may be desirable to incorporate fibres in some parts and not others or else different fibres in different parts. Further, one or more light-absorbing substances may be incorporated in some parts of the solder and not others or the light-absorbing substance may be incorporated at different concentrations throughout one or more parts of the solder. A gradient or profile of the concentration of light-absorbing material can be provided within the solder to control the heat deposition within the solder and avoid excessive thermal tissue damage. The gradient can be created during the preparation of the solder or by painting on a dye solution after solder tube formation. Still further, different parts or the solder may be denatured to different extents. Still further, the solder may be prepared with part of the surface at least partly roughened and part of the surface smooth.

The method may include sterilising the solder after denaturing and before use. Suitable means of sterilisation include gamma ray irradiation, for instance at 2000 rad/min for 50 minutes, autoclaving, steam treatment, heat treatment and gas sterilisation.

Final denaturation of the solder occurs in situ in the tissue, by application of laser or other energy source, where the energy is absorbed by the solder and/or the tissue.

In a fourth aspect the present invention provides a method of repairing a biological tissue comprising the use of a solder of the first aspect in effecting the repair.

The method can be used for effecting repairs in animal as well as human patients.

Typically, the method involves the use of an energy source such as a laser for effecting tissue joins using the solder. Where the energy source is a laser, the selected laser has a wavelength appropriate to any light-absorbing substance used to concentrate the energy at the repair site. The laser chosen should also be appropriate to the tissue being repaired in that the tissue absorbs the energy produced by the laser poorly. For blood vessels, the combination of diode lasers with indocyanine green dye is appropriate. The energy provided should be sufficient to bond the solder to the underlying or overlying tissue while minimising damage to the underlying tissue. The power used will vary for different tissues and can be matched to the amount of energy output required to effect bonding.

The time of treatment for each bond to be effected can vary depending on such factors as ambient conditions, altitude, humidity and the nature of the tissue being joined as well as the moisture level of the tissue being joined.

In one embodiment the invention provides a method for joining body tubes combining the use of a tubular solder of the first aspect and a laser fusion device. The tubular solder can be applied (depending on the physiological tube to be repaired) to either fit inside or outside or inside and outside both the cut ends of the tube. The lasering may be done either directly or through the living tube to the solder to change its characteristics to make it adhesive.

The solder tube can incorporate a light-absorbing material to absorb the wavelength of the laser beam which is applied to form the bond.

Bonding can involve attaching at least one edge of the circumference of the solder tube to the inside or outside of the cylindrical surface of a body tube. The join of the body tube can be completed by placing both ends of the tube within the solder tube and applying energy through the solder to bond the solder to the underlying tissue or by placing both ends of the body tube over the solder tube (FIG. 10) and applying energy through the overlying tissue to the solder or by placing one end of the body tube within the solder tube and one end over the solder tube and applying energy to effect bonding. Where the tube to be repaired includes a damaged section which requires replacement a graft material with solder applied at least at the ends can be joined at either end to a free end of the severed tube (FIG. 9).

Where the tissue repair is with respect to nerve tissue or other tissue tubes where the tube contents need to be protected from damage, it is especially important that the weld should not be concentrated on the edges being joined as this can damage extruded tissue. Rather, the weld should be transverse to the edge of the discontinuity.

The solders of the invention can be used, in conjunction with suitable promoters of neuron growth, in tubular form, to provide guides for nerve regeneration. In this use the severed nerve ends are inserted into the ends of the tube and welded in place.

The solders of the invention can also be used in tubular form with a sealed end as a cap for the ends of severed nerves to assist patients who experience discomfort, which can be extreme, where severed nerves cannot be rejoined, for instance, in amputation stumps.

Where the tissue to be repaired is an essentially wide hollow body tube, the repair can comprise the insertion of a thin-walled hollow cylinder of bio-degradeable solder inside the tube under repair so that the cylinder spans the severed portions of the tube.

End-to-end repairs can also be performed by pulling one end of the repair site through the tube and folding back a cuff of tissue over the tube and then sleeving the other end over the cuff and effecting welds to hold the tube and ends in place. It will be understood that in this particular method it is necessary for the energy source chosen to effect the weld to propagate through the is overlying tissue.

Repairs of tubes in accordance with the invention can include end-to-side as well as end-to-end tubular repairs.

End to side repairs can be performed by providing a tube with a flange at one, end adapted to fit into a x-shaped incision in the side of the tube into which the end is to be inserted. The free tubular end of the solder tube is attached to the end of the tube to be inserted into the x-shaped incision. The sides of the x-shaped incision are welded around the circumference of the solder tube to seal the insertion site. The end-to-side join can be at a variety of angles and thus the flanged portion of the tube can be provided at the appropriate angle for the join to be formed.

The repair methods of the invention may be utilised for joining a diversity of living tubular tissues including arteries, veins, lymphatics, microvessels, any of the body's tubes such as its ducts—pancreatic, liver, cystic, tear, prostatic, and the ureters, urethra, epididymis, vas, fallopian tubes, bowel, bronchi and other gastroenterological and respiratory and body and brain ducts and tubes.

The repair method of the invention can also be applied to the repair of organs and their coverings such as liver, spleen, kidney, uterus, testicles, bladder, cystic, correal, brain and other capsules, coverings and skin and appendages, as well as the various internal and peripheral nerves of the body, the spinal cord and its ramifications by use of at least one appropriately shaped solder of the invention for the repair being made.

The present invention provides a new system of laser-solder-fusion, with or without control of the laser operation which we have demonstrated to be suitable for joining together to produce usual function, in severed living tubes in the rodent, namely arteries, veins, nerves and the vas deferens and bowel. Not only are these severed tubular structures joined without subsequent leakages but they function immediately after joining, those joins are at least eventually as strong and long lasting as is possible with appropriate sutures, they are able to be joined in an exceptionally short time and in addition this is done without inflicting the trauma occasioned by other methods. The system can be adapted co be used through equipment now and in the future developed for minimally invasive therapies.

BEST METHOD OF CARRYING OUT THE INVENTION

1. Preparation of Solder

Figure 1:
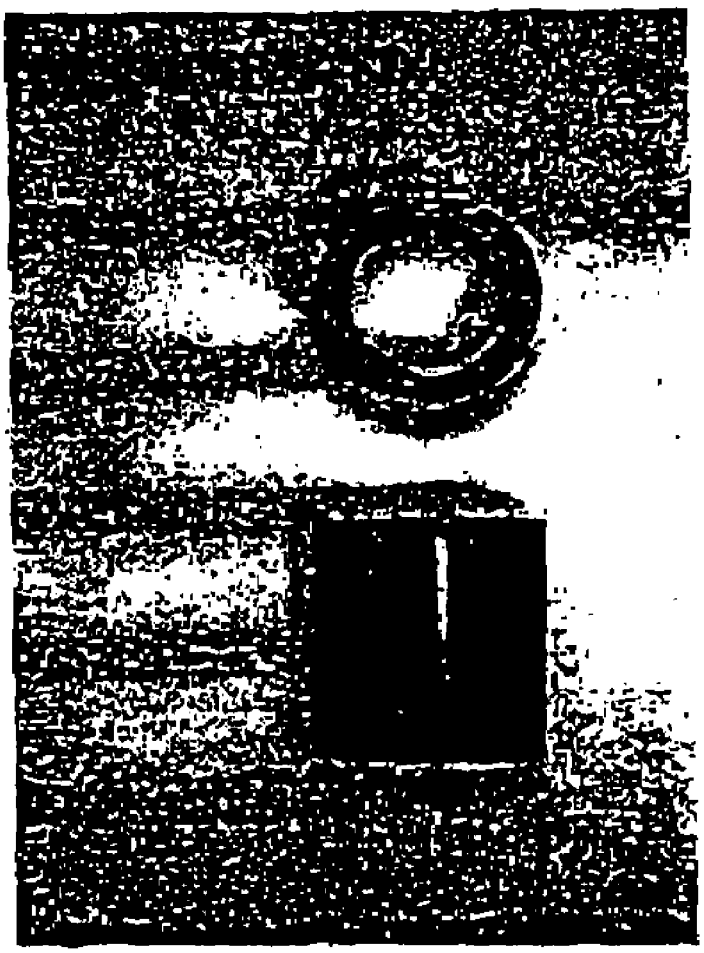
FIG. 1 shows a solid protein cylinder of the invention measuring 2 mm in length and 1.1 mm inner diameter and 1.3 mm outer diameter.

| Starting of Composition: | |
| --- | --- |
| protein | 55–75% (w/w) |
| water | 45–25% (w/w) |
| dye | 0.25% (w/w) |

The protein is bovine, rabbit, human, ovine or rat albumin.
Suitable concentrations for bovine serum albumin include
about 55% and for human and rabbit albumin include about
57% Indocyanine green is a suitable dye. Albumins can be
obtained from Sigma-Aldrich Corporation. Suitable albumin
preparations include:

Bovine albumin—A 2153 Fraction V powder (minimum 96%);

Human albumin—A 1653 Fraction V powder (96–99% albumin);

Rabbit albumin—A 0639 Fraction V powder;

Sheep albumin—A 3264 Fraction V powder;

Horse albumin—A 9888 Fraction V powder.

ovine albumin.

Indocyanine green dye can be obtained from Becton Dickinson Microbiology Systems, Maryland 21030 USA.

A particular formulation for human and rabbit albumin is as follows:

| Starting of Composition: | |
| --- | --- |
| albumin | 57.3% (w/w) |
| water | 42.45% (w/w) |
| ICG dye | 0.25% (w/w) |

Construction:

1. the components (accurately measured) are mixed into a paste form to obtain optimum consistency for extrusion or pressing. For example, the water and dye are first mixed by vortexing to form a consistent dye solution which is then added to the protein followed by mixing to form the paste. Mixing can be performed physically or mechanically and for small batches (<2 g total mass) was performed using a vortex mixer to provide consistency. The solder was not allowed to dry at this stage as this would cause the solder to become brittle and thus unsuitable for extrusion or pressing.

2. The paste can be extruded at this stage but as noted below a superior product can be achieved by deferring final shaping.

3. The extruded paste was then allowed to dehydrate thus increasing the protein concentration and allowing the solder to take a more rigid form.

4. The rigid solder was immersed in hot water at 80–90° C. (for example 85° C. for bovine albumin) for approximately 1 minute to denature the protein. Where the solder is prepared from human or rabbit albumin the relevant treatment is with steam at about 120° C. for 10 minutes (it is envisaged that the temperature could be as low as 100° C. or up to 150° C.). This denaturation treatment causes the solder to bond within itself and the solder becomes less soluble in water.

5. The solder at this stage is elastic and may be further cut into desired shapes easily without inducing stress or fracture. Desired shapes include sheets, tubes, partial tubes and rods. If cut to shape before step 4, the solder may fracture through the presence of crystalline structure if it is too dry or else it may deform if it is too moist.

6. The solder is preferably dehydrated at this stage and gamma irradiated or autoclaved for sterilisation and stored in a dry, sterile and light proof container.

A particular protocol that has been used successfully with the human or rabbit serum albumin formulation mentioned above is:

1. mix the protein preparation 2. extrude the preparation 3. allow the preparation to dry 4. autoclave the preparation at 120° C. for 10 minutes.

2. Method of Repair

The following repairs have been effected:

| | |
| --- | --- |
| Rat aorta: | 1.3 mm diameter |
| cylinder used: | 1.4 mm internal diameter |
| | 1.7 mm external diameter, |
| | 2 mm length |
| Rabbit femoral artery: | 2 mm diameter |
| Cylinder used: | 1.6 mm internal diameter |
| | 2.1 mm external diameter |
| | 2 mm length |

Joining tubes can involve attaching at least one edge of the circumference of a solder tube to the inside or outside of the cylindrical surface of a body tube. The join of the body tube can be completed by placing both ends of the tube within the solder tube and applying energy through the solder to bond the solder to the underlying tissue or by placing both ends of the body tube over the solder tube and applying energy through the overlying tissue to the solder or by placing one end of the body tube within the solder tube and one end over the solder tube and applying energy to effect bonding. Where the body tube to be repaired includes a damaged section which requires replacement a graft material with solder applied at least at the ends can be joined at either end to a free end of the severed tube.

Where the tissue repair is with respect to nerve tissue or other tissue tubes where the tube contents need to be protected from damage, it is especially important that the weld should not be concentrated on the edges being joined as this can damage extruded tissue. Rather, the weld should be transverse to the edge of the discontinuity.

End to side repairs can be performed by providing a tube with a flange at one end adapted to fit into a x-shaped incision in the side of the tube into which the end is to be inserted. The free tubular end of the solder tube is attached to the end of the tube to be inserted into the x-shaped incision. The sides of the x-shaped incision are welded around the circumference of the solder tube to seal the insertion site. The end-to-side join can be at a variety of angles and thus the flanged portion of the tube can be provided at the appropriate angle for the join to be formed.

End-to-side repairs can also be performed by providing a partial solder tube with a flange adapted to fit over a longitudinal incision in the side of the body tube onto which the new tubular end is to be attached. The sides of the longitudinal incision are pulled through the solder flange, everted around the flange and welded to the outside of the solder flange. The free end of the side branch is then pulled over the previously welded body tube and flange and welded to the main body of the partial solder tube. The main body of the partial solder tube is then welded to the outside of the main body tube. The end-to-side join can be at a number of angles and thus the flanged portion of the tube can be provided at the appropriate angle.

Repairs of non-tubular tissues are effected by using at least one appropriately shaped solder of the invention together with an energy source to effect bonding between solder and tissue.

3. Description of Sleeve Method

Figure 2:
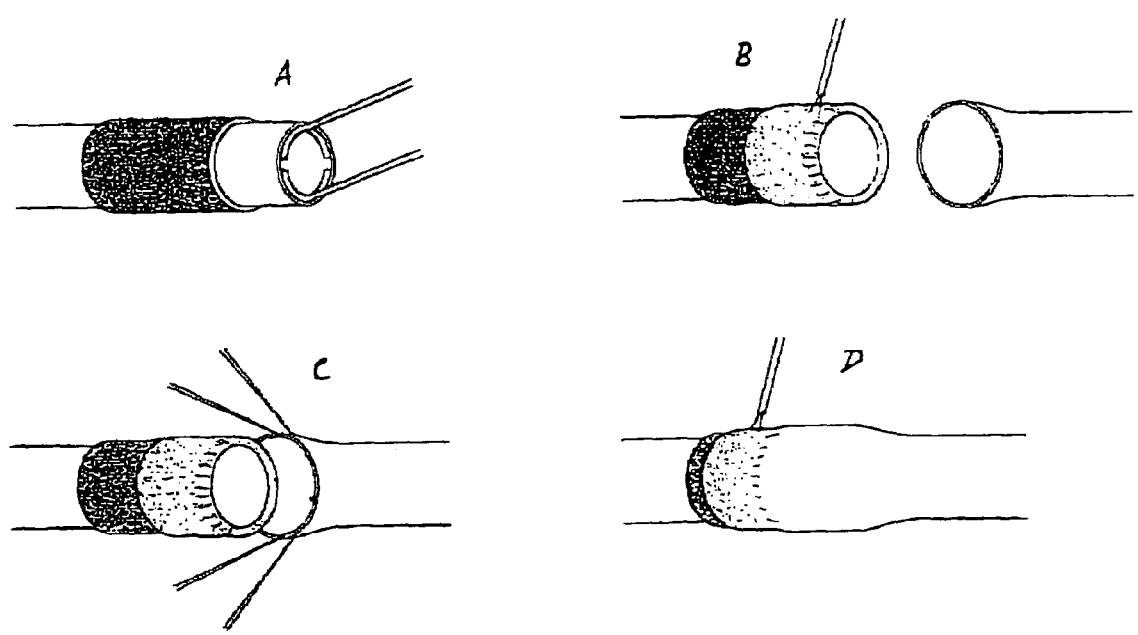
FIG. 2 shows a schema of an operative technique of the fourth aspect of the invention: (A) The solder is pushed over the proximal vessel end and the vessel wall is pulled back. (B) Laser energy application at the distal part of the solder. (C) The distal end of the vessel is gently pulled over the entire length of the solder. (D) Laser energy application to the proximal part of the solder.
Figure 3A:
FIG. 3 shows the appearance of the laser welded microanastomosis immediately after clamp release (A) and after 6 weeks (B).
Figure 3A:
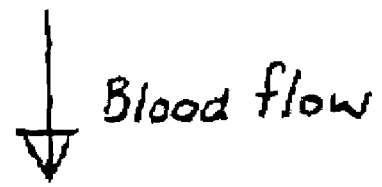
Figure 3B:
Figure 3B:

The proximal artery (tube) is pulled through a tube of solder and turned back on itself a short distance using purpose built forceps, which have ends adapted to provide a surface which functions to maintain the tube end in open form, such as the forceps illustrated in FIG. 2. The overlapping turned back artery is lasered to an observable slight change in colour and specific temperature, which denatures the protein and causes it to adhere to the vessel wall on both or at least one side in a circle around the proposed join area. The distal artery (or tube) is slightly stretched and manipulated gently over the already lasered area and beyond to the as yet unlasered solder tube of equal lasing area. This area is then lasered in the same way and causes that circular portion of the artery to be lasered to the cylinder. That completes the join.

EXAMPLE 1

A total of 90 rats were divided into two groups randomly. In group one the anastomoses were performed using conventional microsuturing technique, while in group two the anastomoses were performed using our new laser welding technique. In addition, each of the two groups were divided into 5 subgroups and evaluated at different followup periods (10 min, 1 hour, 1 day, 1 week and 6 weeks). At these intervals the anastomoses were evaluated for patency and strength (tensile strength measurement) anastomoses in each subgroup were processed for light and electron microscopy.

All anastomoses were found to be patent. The mean clamp time of the anastomoses performed with conventional suturing was 20.6 minutes compared to 7.2 minutes for the laser activated welded anastomoses ($p<0.001$). The strain measurements showed a stronger mechanical bond of the sutured anastomoses in the initial phase. However, at 6 weeks the tensile strength of the laser welded anastomoses was higher compared to the conventional suture technique. Histologic evaluations revealed a near complete resorption of the solder after six weeks. The junction site of the vessel ends could not be determined on the luminal side of the artery.

In conclusion, a resorbable protein used as a solder, activated by a diode laser, can provide a reliable, safe and rapid arterial anastomosis, which could be performed by any microsurgeon faster than conventional suturing after a short learning curve.

Simplifying vascular anastomoses in surgery and in particular in small diameter vessels has been an important topic in the past. A recent publication reviewed the technical developments in this field since the start of this century [1]. Minimising foreign body reaction at the anastomotic site has been an important issue, and a variety of authors have described the negative impact of suture materials, staples and clips on vessel wall compliance and active force production [2–6]. The use of laser welding techniques for vascular anastomosis has first been reported by Jain in 1979 [7, 8]. Different types of lasers hare been used [9–12] in order to minimise the potential negative impact on tissues. Most reported techniques require at least three permanent stay sutures and therefore laser welding was used only to seal the vessel and not to mechanically hold the vessel ends together. The use of lasers to weld tissue relies on the efficient deposition of heat due to the light absorbed by the tissue. The laser wavelengths that have been used thus correspond to strong absorption bands of water, hemoglobin or other tissue chromatophores. The introduction of dyes such as indocyanine green [13, 14] or fluorescein isothiocyanate [15] enhances the delivery of the laser energy precisely to the target tissues. In addition, the application of laser activated protein solders has been shown to strengthen laser welds in tissues such as nerves [16–18]. Our study presents a sutureless, quick and reliable technique to successfully anastomose small diameter arteries, avoiding vessel wall fibrosis by eliminating any permanent implanted devices. We combined an anastomotic technique reported by Payr in 1900 [19] with the use of a fully biodegradeable, diode-laser-activated protein tube to weld small diameter arteries.

Materials and Methods

A total of 90 young adult male Wistar rats (outbred) weighing 450 to 550 g were used in this study. Consent and approval for this investigation were obtained from our Institution's Animal Ethical Review Committee. All surgical procedures were performed under general anaesthesia with a halothane/oxygen mix (4% halothane at 4 L/min oxygen for inducing and 2% halothane at 2 L/min oxygen for maintaining anaesthesia). Clean, but not aseptic conditions were maintained during the surgical procedures, which were performed using a Zeiss OPMI 7 operating microscope. A midline laparotomy was performed and the infrarenal aorta exposed, incising the peritoneum, freeing the tissues and ligating lumbar and ileolumbar vessels if necessary. A double microvascular clamp (Edward Weck Inc. micro vessel approximator 1.5 mm×8.0 mm blades, 19 mm bar) was applied to the aorta, which was severed with straight microscissors. After flushing the two stumps with saline, connective tissue in excess was removed, but leaving the adventitia intact. In 45 animals the anastomoses were carried out by conventional microsuturing (9/0 Nylon with a 140 u needle, 10 to 12 interrupted sutures) and in the remaining 45 animals the anastomoses were performed by laser welding. The clasp time of all procedures was recorded for later statistical analysis with the students t-test. No local or systemic anticoagulant drugs were used, nor were the animals given antibiotics post-operatively.

Laser Welding

A GaAlAs laser diode with a nominal power of 250 mW and wavelength of 805 nm (Spectra Diode Labs Inc., San Jose Calif.) was used. The laser radiation was coupled into a 100 um diameter core, numerical aperture (NA 0.28) optical fiber, which was held by hand in a fiber chuck. The diode current and temperature were controlled by a SDL-800 diode driver. The diode was operated by a foot switch and was set at 90 mW during surgery, with a spot size at the tissue of 200 um diameter, corresponding to a maximum irradiance of 286 W/cm$^2$ at the tissue surface. The laser power was measured with a Scientech power meter (Boulder Inc., CO USA). The total irradiation time for each circular weld was 10 sec approximately.

The solder used in this study was a mixture of water, concentrated bovine serum albumin and indocyanine green (ICG) dye (Becton Dickinson, Maryland USA). ICG has a maximum absorption coefficient at a wavelength of 805 nm of $2 \times 10^5 M^{-1} cm^{-1}$. ICG binds preferentially with serum proteins such as albumin [20] ensuring that the heat is efficiently transferred to denature the protein solder. A high protein concentration mixture (55.40% albumin: 44.33% water: 0.27% ICG by weight starting material) was obtained by vigorous stirring of the components. The mixture was formed into tubes suited to the dimensions of a rat aorta. The solder tubes were predenatured to make them more flexible and chemically stable (FIG. 1).

The solid protein tube was then used in a way similar to that described by Payr in 1900 when using absorbable magnesium rings [19], (FIG. 2). The proximal vessel was passed through the cylinder, everted over the edge for a length of 1 mm and then welded to the protein cylinder by means of laser energy, further denaturating the protein contained in the solder (FIGS. 2A, B). Laser energy was delivered by an optical hand-held fiber for a period of time according to the tissue reaction visible through the operating microscope (approximately 10 sec/circumference). When the slightest retraction of the tissue was noted the laser spot was moved to adjacent tissue until the total circumference of the vessel was welded onto the protein cylinder. The two branches of the double clamp were then approximated and the distal vessel was gently pulled over the entire protein cylinder (FIG. 2C). Laser energy was then applied to create a bond between the distal end of the artery and the most proximal part of the solder (FIG. 2D).

Immediately after removing the clamps the anastomoses were examined to assess patency by the milking test. Each group was then divided into 5 subgroups to be reevaluated at different intervals (10 minutes, 1 hour, 1 day, 1 week, 6 weeks) with 9 animals per subgroup. At the chosen time all anastomoses were re-exposed and patency was checked with the milking test. In 6 animals per subgroup the anastomotic sites together with 5 mm of vessel proximally and distally were removed and subjected to tensile strength measurements. These were performed by attaching one end of the vessel to a calibrated force transducer (FT30C, Grass Instruments, Quincy, Mass.) and the other end to a screw driven translator [18]. In 3 animals per subgroup the vessels were clamped, flushed with saline and fixative (5% glutaraldehyde buffered to pH 7.4) and finally removed for histology. Staining for light microscopy was done with Masson's trichrome to clearly differentiate native protein from denatured protein and with Toluidine Blue. Scanning electron microscopy was used to study the inner surfaces of the anastomoses.

Results

All animals survived the surgical procedure and all anastomoses were patent at the time of re-exploration. At 6 weeks there were no aneurysms at the site of the sutured or laser welded anastamoses (FIG. 3).

The mean clamp time of the sutured anastamoses was 20.6 minutes (SD 2.82, SEM 0.52) which was significantly longer than the mean clamp time of the laser welded anastomoses, 7.2 minutes. (SD 2.26, SEM 0.41), (p<0.001; students t-test).

Figure 4:
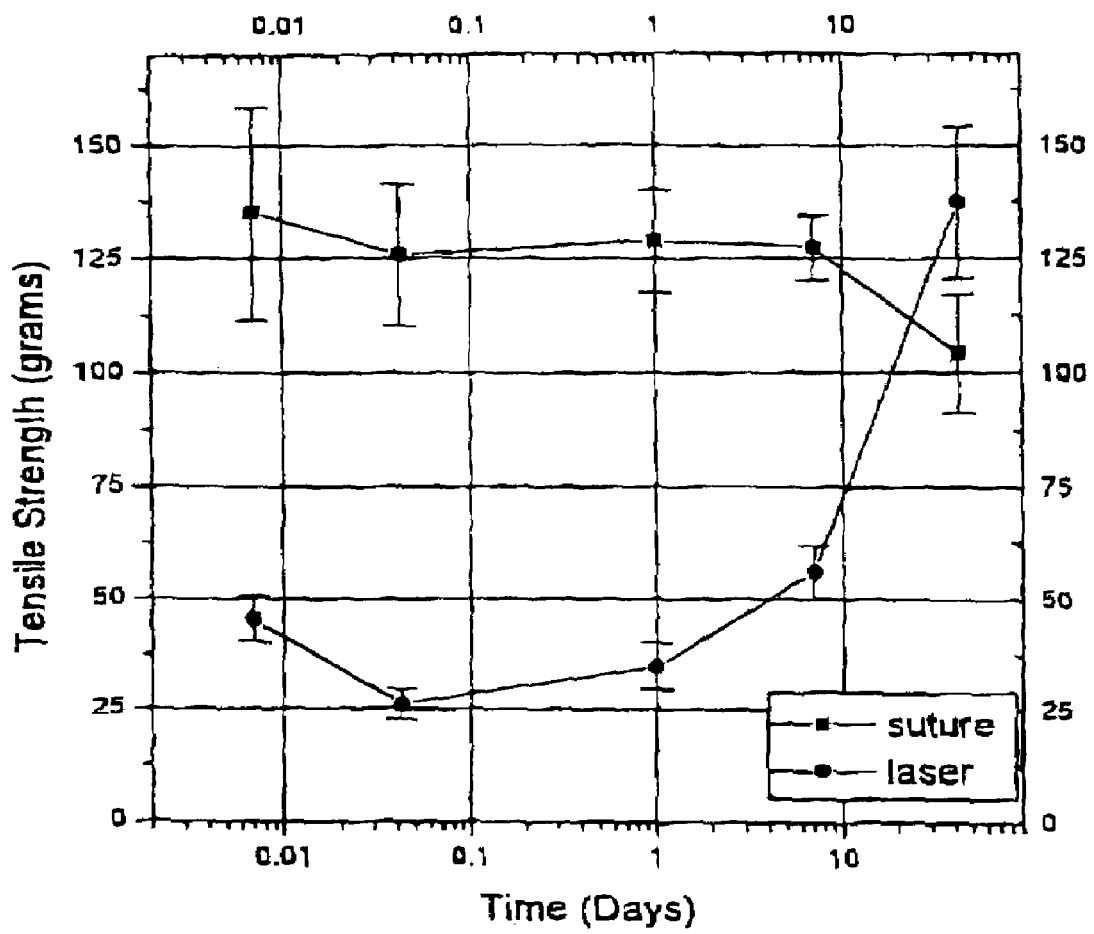
FIG. 4 shows graphic representation of tensile strength of suture and laser solder anastomoses of rat aortas as a function of time after surgery. (time is on logarithmic scale)
Figure 5A:
FIG. 5 shows a laser-welded anastomosis in longitudinal section immediately after laser irradiation. (Masson's trichrome, (A) arrow indicates direction of blood flow. 5×
magnification and (B) 50× magnification)
Figure 5A:
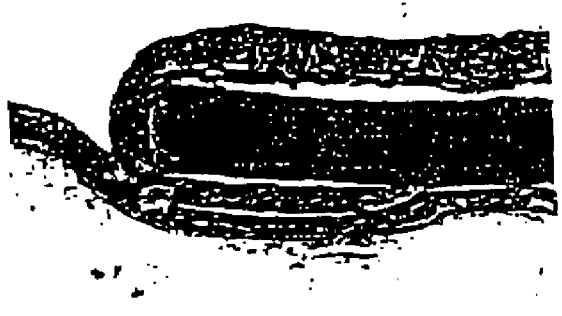
Figure 5A:
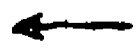
Figure 5B:
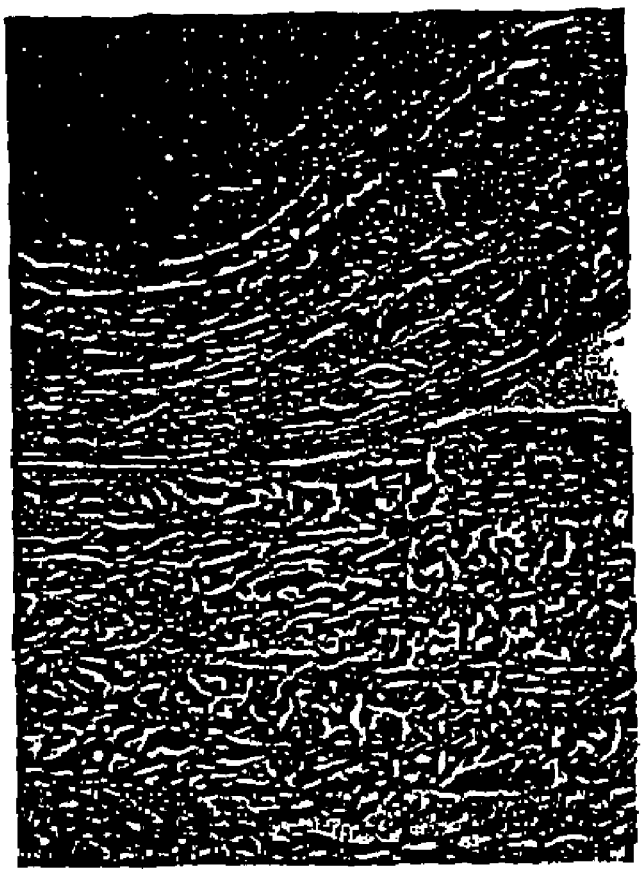

Tensile strength measurements revealed that the sutured anastomoses were stronger (under stress) when compared to the laser-welded anastomoses in the short term (134.6 gm and 45.3 gm respectively). However, at 6 weeks the tensile strength for the laser welded anastomoses was slightly higher in comparison to the sutured anastomoses (134.2 gm and 103.9 gm respectively, p=0.005, student's t-test) (FIG. 4) The sutured anastomoses, when subjected to traction, ruptured at the junction level tearing a small cuff off the vessel wall, while the laser-welded vessels detached at the distal portion of the bond, probably the weakest point of the anastomosis.

Figure 6:
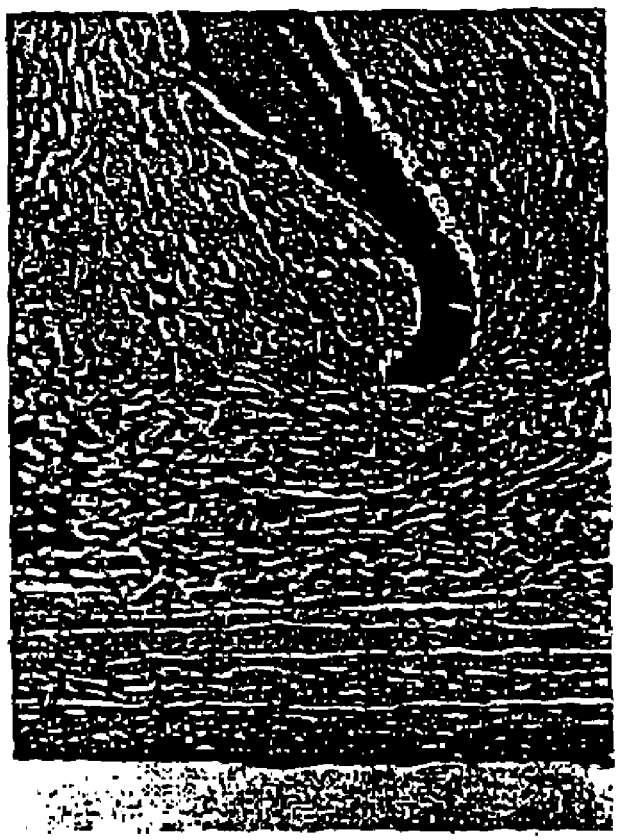
FIG. 6 shows the remains of solder in the vessel wall after
6 weeks. Note the normal appearance of the intima and
media. Note the presence of phagocytotic cells at the solder
surface. (Toluldine Blue, magnification 20×)
Figure 7:
FIG. 7 shows scanning electron micrographs of the lumen
of the laser welded anastomosis 10 minutes after reestablishing perfusion (longitudinal section). (magnification×
100).
Figure 8:
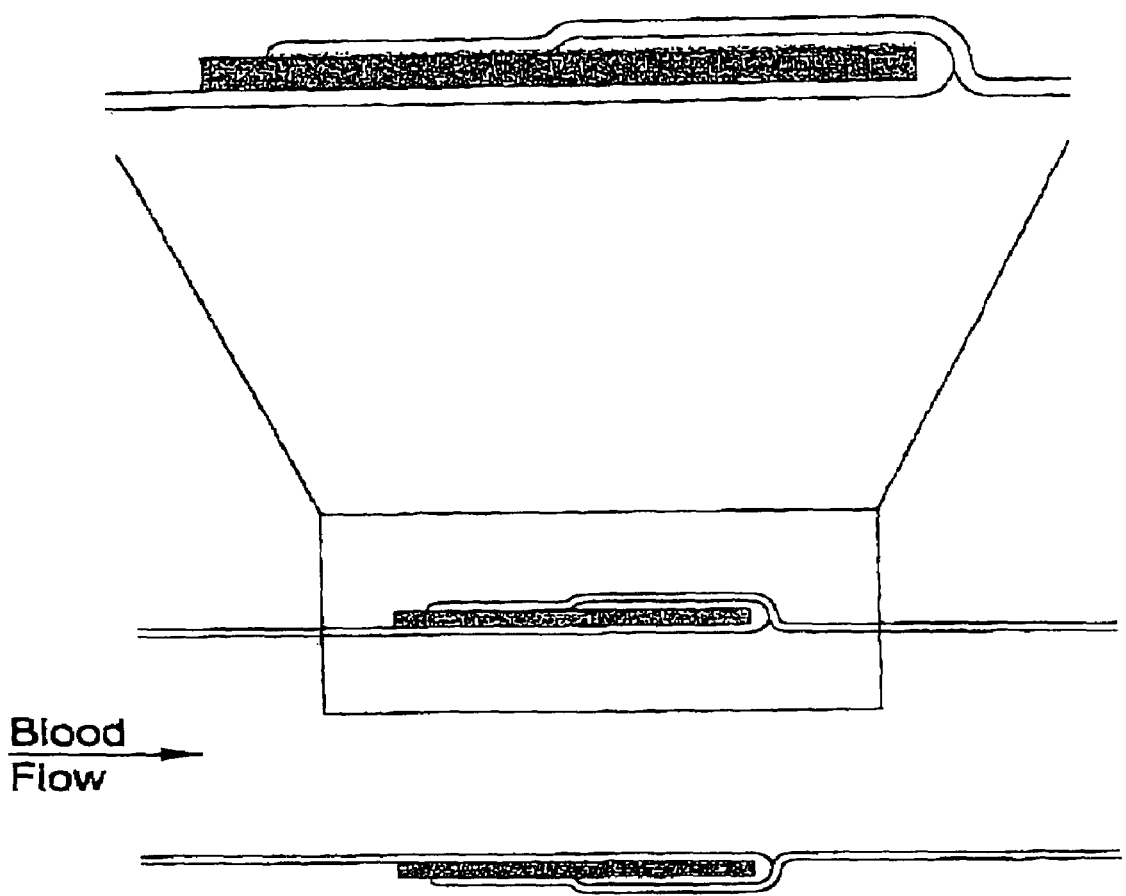
FIG. 8 is a schematic cross section of an anastomosis of
a blood vessel formed using the sleeve technique.
Figure 9:
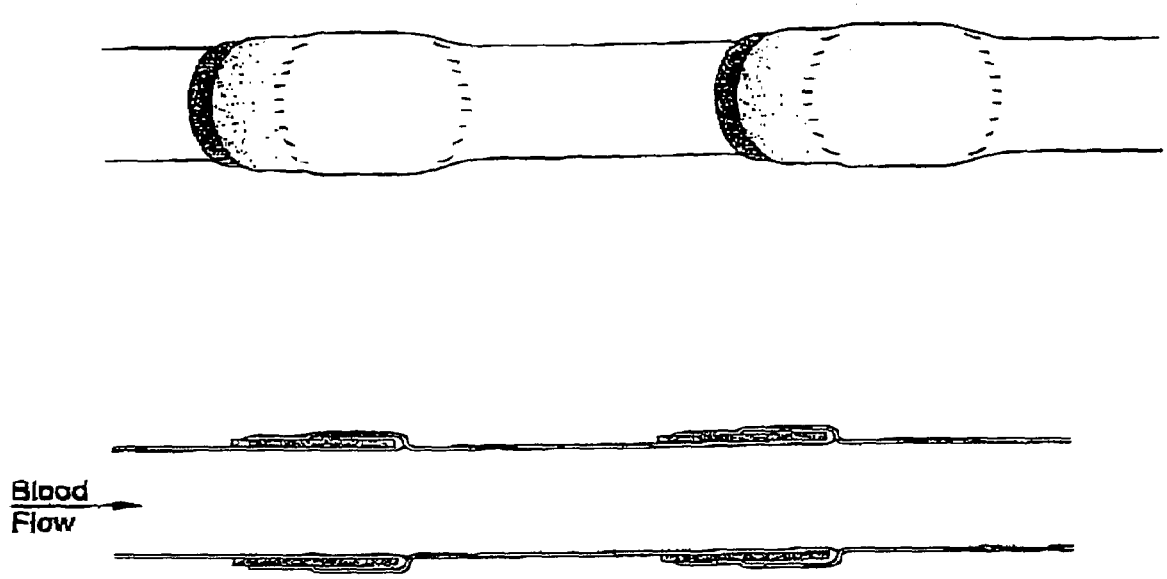
FIG. 9 shows a graft in side and cross sectional view
formed using the sleeve technique of the fourth aspect of the
invention at both ends of the graft.
Figure 10:
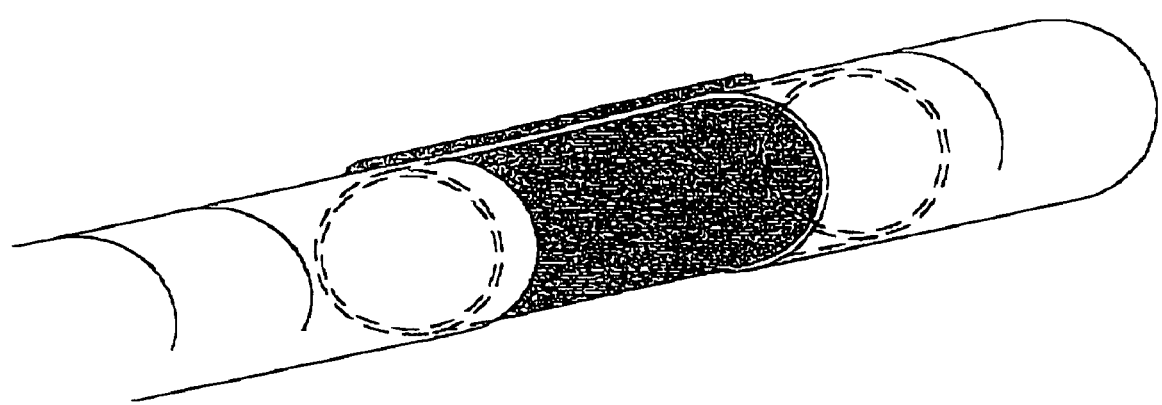
FIG. 10 shows in schematic form, a join formed by
placing a solder tube of the invention inside a body tube.
Solder strips may be used externally to strengthen the
anastomosis.

Light microscopy evaluation after staining of the anastomotic site immediately after laser application with Masson's trichrome revealed denaturated protein in the layer directly adjacent to the solder, but no changes could be observed in the media of the artery (FIG. 5). After 6 weeks the solder was almost completely resorbed and the intimal layer could be observed in continuity. Healing occurred with proliferation of myofibroblasts and the site of the anastomosis could not be detected from the lumen of the artery (FIG. 6). However, some fibrotic reaction could be seen on the adventitia as shown in FIG. 3b, but again the media of the artery did not reveal any changes. Scanning electron microscopy of the anastomotic site after perfusion was reestablished for 10 minutes showed some red blood cell deposition at the site of the anastomosis, but this did not have any impact on patency (FIG. 7).

Discussion

Since Jain's first report on the successful use of laser energy for the repair of blood vessels [7], there have been numerous attempts to develop a technique for sutureless anastomosis of blood vessels employing laser welding. The advantages of laser welding have been shown to be due to a perfect seal of the junction with no leakage and less foreign body reaction due to less suture material. However, the need for stay sutures to maintain vessel end approximation has led to the term laser-assisted anastomosis [21–25], where the laser is used to seal an anastomosis after three to five stay sutures have been previously inserted. On the other hand, true sutureless anastomoses have been performed by using an intraluminal stent to ensure intimal alignment [26–28]. These stents have mostly been designed to be intraluminally absorbed and therefore may potentially lead to arterial embolism and/or thrombosis. A previously reported technique to repair tubular structures [18] employs protein solder bands containing indocyanine green dye, which were designed to absorb the laser energy and therefore heat was localized at the protein solder and the immediate surrounding tissue.

Changes in the tissue due to heating caused by the laser energy were observed only in the tissue layer in immediate contact with the solder. In order to get optimal intimal alignment, which is crucial for successful microvascular anastomosis, the protein solder was extruded into a tube with corresponding diameters to the vessel to be repaired. The optimal intimal alignment was accomplished by employing a technique introduced by Payr at the turn of the century [19]. This technique was further developed by Landon [29] eliminating the need for ligatures to secure the vessel onto the ring and by Carter [30] for coronary artery surgery using a polyethylene ring. Haller [31] reported a 92% patency rate in the anastomosis of 4-mm diameter vessels using Payr's technique with tantalum rings. This technique prevents the blood coming in contact with the protein solder which eliminates the risk that the coagulation cascade is activated and leads to smooth intimal alignment. The laser welding technique causes the tissue to bond to the protein solder tube by means of protein denaturation in the tissue and the solder.

In earlier studies the actual mechanism of the bond created by laser welding has been identified as the possible homogenisation of the adventitia as well as coagulation necrosis of smooth muscle cells, however the elastic lamellae were unaltered [32]. In a direct laser welding study, protein denaturation of the collagen fibers was observed with electron microscopy, with a slight interruption of the intima and subsequent re-endothelialization within 10 days [33]. Dehydration of the triple helix molecular structure of collagen present in the arterial wall breaking Van der Waal's bonds, which subsequently re-form to other collagen molecules, was reported as a possible bonding mechanism [34]. Our technique confines the laser-induced changes in the artery wall to the layer directly in contact with the protein solder, thus minimizing any weakening of the vessel wall. In particular neither the proximal nor distal vessels' tunica media were altered by the laser energy as shown by histologic evaluation. It may then be suggested, that by this technique the arterial wall is only minimally altered and does not lose its mechanical properties. After healing of the anastomotic site the tensile strength measurements revealed better results for the laser-welded anastomoses compared to the sutured anastomoses, which could be a result of the fibrous reaction to the suture material in the tunica media.

REFERENCES

1) Werker P M N, Kon M. Review of facilitated approaches to vascular anastamosis surgery. Ann. Thorac. Surg. 63:S122, 1997.
2) Serure A, Withers E H, Thomson S, Morris J. Comparison of carbon dioxide laser-assisted microvascular anastomosis and conventional microvascular sutured anastomosis. Surg. Forum. 34:634, 1983.
3) Lidman D, Daniels R K. The normal healing process of microvascular anastomoses. Scan. J. Plast. Surg. 15:103, 1981.
4) Servant J, Ikuta Y, Harada Y. A scanning electron microscope study of microvascular anastomoses Plast. Reconstr. Surg. 57:329, 1976.
5) Acland R D, Trachtenberg L The histopathology of small arteries following experimental microvascular anastomosis. Plast Reconstr. Surg. 59:868, 1977
6) Dalsing M C, Packer S C, Kueppers P, Griffith S L, Davis T B. Laser and suture anastomosis: Passive compliance and active force production. Lasers Surg. Med. 12:190, 1992.
7) Jain K K, Gorisch W. Repair of small blood vessels with the Neodymium-Yag laser. A preliminary report Surgery 51:684, 1979.
8) Jain K K, Gorisch W. Microvascular repair with Neodymium-Yag laser. Acta Neurochir. (Wien) Suppl. 28:260, 1979.
9) White R A, Abergel R P, Lyons R, Klein S R, Kopchok G, Dweyer R M, Uitto J. Biological effects of laser welding on vascular healing. Lasers Surg. Med. 6:137, 1986.
10) Kopchok G E, White R A, White G H, Fujitani R, Vlasak J, Dykhovsky L, Grundfest W S. $CO_2$ and argon laser vascular welding. Acute histologic and thermodynamic comparison Lasers Surg. Med. 8:584, 1988.
11) Nakata S. Campbell C D, Pick R, Replogle R L. End-to-side and end-to-end vascular anastomoses with a carbon dioxide laser J. Thorac. Cardiovasc. Surg. 98:57, 1989.
12) Lewis W J. Uribe A. Contact diode laser Microvascular anastomosis. Laryngosc. 103:850, 1993.
13) Reali T M, Gelli R, Gianotti V, Clori F, Pratesi R, Pini R. Experimental diode laser-assisted microvascular anastomosis. J. Reconstr. Microsurg 3:203, 1993.
14) Oz, M C, Johnson J P, Paranagi S, Chuck R S, Marboe C C, Bass L S, Nowygrod R, Treat M R. Tissue soldering by use of indocyanine green dye-enhanced fibrinogen with near infrared diode laser. J. Vasc. Surg. 11:718, 1990.
15) Chuck R S, OZ M C, Delohery T M, Johnson J P, Bass L S, Nowygrod R, Treat M R. Dye-enhanced laser tissue welding. Laser Surg. Med. 9:471, 1989.
16) Bass L S, Moazami N, Avellino A, Trosaborg W, Treat M R. Feasibility studies for laser solder neuro-rhaphy. Proc SPIE 2128:472, 1994.
17) Menovsky T, Beek J F, van Gemert M J C. $CO_2$ laser nerve welding optimal laser parameter and the use of solders in vitro. Microsurg. 15, 44, 1994.
18) Lauto A, Trickett R, Malik R, Dawes J M, Owen E R. Laser-activated solid protein bands for peripheral nerve repair. An in vivo study. Laser Surg. Med. 21:13 4, 1997.
19) Payr E. Beitraege zur Technique der Blutgefaessund Nervennaht nebst Mittellungen ueber die Verwendung eines resorblerbaren Metalles in der Chirurgle. Arch. Klin. Chir. 62:67, 1900.
20) Sauda K, Imasaka T, Ishibashi N. Determination of protein in human scrum by high performance liquid chromatography. Analytical Chemistry 58: 2649, 1986.
21) McCarthy WJ, LoCicero J, Hartz R S, Yao J S T. Patency of laser-assisted anastomoses in small vessels: Oneyear follow-up. Surgery 102.319, 1987.
22) Okada M, Shimizu K, Ikuta Horii H, Nakamura K. An alternative method of vascular anastomosis by laser: experimental and clinical study. Laser Surg. Med. 7:240, 1987.
23) Abrahamson D L, Shaw W W, Kamat B R, Harper A, Rosenberg C R. Laser-assisted venous, anastomosis: A comparison study. J. Reconstr. Microsurg. 7:199, 1991.
24) Kiyoshige Y, Tsuchida H, Hamasaki M, Takayanagi M, Watanabe Y. $CO_2$ laser-assisted microvascular anastomosis: Biomechanical studies and clinical applications. J. Reconstr. Microsurg. 7:225, 1991.

25) Tang J. Godlewski G, Rouy S, Dauzat M, Juan J M, Chambettaz F, Salathe R. Microarterial anastomosis using a noncontact diode laser verses a control study. *Users Surg. Med.* 14:229, 1994.

26) Jain K K. Sutureless microvascular anastomosis using a Neodymium-YAG laser. *J. Microsurg.* 1:436, 1980.

27) Niijima K H, Yonekawa Y, Handa H, Taki W. Nonsuture microvasular anastomosis using an Nd-YAG laser and a water-soluble polyvinyl alcohol splint. J. Neurosurg. 67:579, 1987.

28) Bass L S, Treat M R, Dzakonski C, Trokel S L. Sutureless microvasular anastomosis using the THC:YAG laser. A preliminary report. Microsurg. 10: 189, 1989.

29) Landon L H. A simplified method of direct blood transfusion with self retaining tubes. JAMA 61:490, 1913.

30) Carter E L, Roth Ej. Direct non-suture coronary anastomosis in the dog. *Ann. Surg.* 148:212, 1958.

31) Haller J D, Kripke D C, Rosenak S S, Roberts D R, Rohman M. Long-term results of small vessel anastomoses with a ring technique. Ann. Surg. 161:67, 1965.

32) Schober R, Ulrich F, Sander T, Duerselen H, Hessel S. Laser-induced alteration of collagen substructure allows microsurgical tissue welding. Science 232:1421, 1986.

33) Godlewski G, Rouy S, Dauzat M. Ultrastructural study of arterial wall repair after argon laser micro-anastomosis. Lasers Surg. Med. 7:258, 1987.

34) Fenner J, Martin W, Moseley H, Wheatley Dj. Shear strength of tissue bonds as a function of bonding temperature: a proposed mechanism for laser-assisted tissue welding. Lasers Med Science 7:39, 1992.

The invention claimed is:

1. A biomolecular solder made by a method comprising
   (b) providing a composition comprising a proteinaceous substance in a solvent; and
   (b) pre-denaturing the proteinaceous substance before placing the composition in situ by at least partially denaturing the proteinaceous substance while moist with the solvent such that at least a portion of the proteinaceous substance bonds together.

2. A solder according to claim 1 wherein the proteinaceous substance comprises a protein.

3. A solder according to claim 2 wherein the protein comprises an albumin, a collagen an elastin, a fibrinogen, or any combination thereof.

4. A solder according to claim 1, further comprising a dye.

5. A solder according to claim 4 wherein the dye comprises an indocyanine green, a methylene blue or a fluorescein isothiocyanate or any combination thereof.

6. A solder according to claim 1, further comprising an adjuvant.

7. A solder according to claim 1 further comprising a growth factor, a sodium hyaluronate, a hormone and an anti-coagulant.

8. A solder according to claim 1 further comprising a material for improving the strength of the solder.

9. A solder according to claim 8 wherein the material comprises a polytetrafluoroethylene fibre or a ceramic fibre.

10. A kit comprising a biomolecular solder according to claim 1.

11. A method of preparing a biomolecular solder ex vivo, the method comprising:
    (a) providing a composition comprising a proteinaceous substance and a solvent;
    (b) shaping the composition into a desired shape, wherein the composition is shaped before, during or after the pre-denaturing of step (c), or a combination thereof; and
    (c) pre-denaturing the proteinaceous substance before placing the composition in situ by at least partially denaturing the proteinaceous substance while the composition is moist such that at least a portion of the proteinaceous substance bonds together, thereby preparing a biomolecular solder.

12. A method according to claim 11 wherein the proteinaceous substance is pre-denatured by exposing the solder to an energy for a time period that is sufficient to allow the energy to at least partially denature the proteinaceous substance.

13. A method according to claim 12 wherein the energy comprises a thermal energy.

14. A method according to claim 13 wherein the proteinaceous substance is pre-denatured by heating the solder at a temperature of greater than 40° C. for a time period of about 30 seconds or longer.

15. A method according to claim 14 wherein in the pre-denaturing step the solder is heated in a hot liquid bath or in pressurized steam.

16. A method according to claim 11 wherein the proteinaceous substance is pre-denatured by exposure to a denaturing agent for a time period that is sufficient to allow the denaturing agent to homogenously and completely denature the proteinaceous substance.

17. A method according to claim 11 wherein the biomolecular solder further comprises a dye.

18. A method according to claim 17 wherein the dye is in an amount between 0.1 to 2.5% w/w of the solder.

19. A method according to claim 17 wherein the dye is mixed with the solvent, prior to mixing the solvent with the proteinaceous substance.

20. A method according to claim 11 wherein the pre-denaturing step further comprises drying the composition, wherein a majority of the solvent is removed from the composition during the drying of the composition.

21. The method of claim 11 wherein in the pre-denaturing step the composition is applied to a support structure before the proteinaceous substance is pre-denatured.

22. The method of claim 21 wherein the support structure is a mesh, a stiffener or a graft material.

23. The method of claim 11 further comprising the step of sterilizing the biomolecular solder following the pre-denaturing of the proteinaceous substance.

24. A method of welding or joining a biological tissue together, the method comprising:
    (a) applying a biomolecular solder according to claim 1 to the biological tissue to be welded or joined together; and
    (b) exposing the biomolecular solder to an energy for a time sufficient to cause the solder to weld or join the biological tissue together.

25. The method of claim 24 wherein the pre-denatured solder is moistened before application to the biological tissue.

26. The biomolecular solder of claim 1 wherein the proteinaceous substance is denatured ex vivo such that it is essentially insoluble in the physiological fluid at body temperature.

27. The biomolecular solder of claim 1 wherein the pre-denatured solder has been shaped from a composition comprising the proteinaceous substance in an amount of at least 40% w/w of the composition.

28. The biomolecular solder of claim 1 wherein the proteinaceous substance comprises at least one substance selected from the group consisting of a protein, a polypeptide, a mixture of proteins, a biodegradable protein, a fibrous material, a synthetic polypeptide and any combination thereof.

29. The method of claim 11 further comprising drying the pre-denatured solder.

30. The method of claim 11 wherein the pre-denatured solder, shaped into the predetermined shape, comprises the proteinaceous substance in an amount of at least 40% w/w or greater of the solder.

31. The method of claim 11, wherein the solder initially comprises a proteinaceous substance in an amount in the range from 50% w/w to 80% w/w of the solder.

32. The method of claim 30 or 31 wherein the solder initially comprises a solvent in an amount up to 60% w/w of the solder.

33. The method of claim 11 wherein the pre-denaturing step comprises heating the solder at a temperature in a range from between about 75° C. to 100° C.

34. The method of claim 33 wherein the pre-denaturing step comprises heating the solder at a temperature in a range from between about 100° C. to 150° C.

35. The method of claim 16 wherein in the pre-denaturing step the denaturing agent comprises a chemical.

36. The method of claim 11, wherein the proteinaceous substance comprises at least one substance selected from the group consisting of a protein, a polypeptide, a mixture of proteins, a biodegradable protein, a fibrous material, a synthetic polypeptide and any combination thereof.

37. The method of to claim 36 wherein the proteinaceous substance comprises at least one substance selected from the group consisting of human albumin, bovine albumin, horse albumin, ovine albumin, rabbit albumin, rat albumin, and a combination thereof.

38. The method of claim 36, wherein the proteinaceous substance comprises at least one protein selected from the group consisting of an albumin, an elastin, a collagen and a fibrinogen.

39. The method of claim 25 wherein the moistening of the pre-denatured solder increases flexibility of the solder.

40. The biomolecular solder of claim 1, wherein the solvent comprises an aqueous solvent.

41. The biomolecular solder of claim 40, wherein the aqueous solvent comprises water or saline.

42. The method of claim 11, wherein the solvent comprises an aqueous solvent.

43. The method of claim 42, wherein the aqueous solvent comprises water or saline.

44. The method of claim 11, wherein denaturing the protein in situ in step (e) comprises denaturing the proteinaceous substance by exposing the solder to a laser energy.

45. The method of claim 44, wherein the laser is a diode laser.

46. The method of claim 24, wherein the biological tissue is welded together to effect a repair.

47. The biomolecular solder of claim 1, wherein denaturing the protein in situ in step (e) comprises denaturing all of the proteinaceous substance.

48. The biomolecular solder of claim 1, wherein denaturing the protein in situ in step (e) comprises denaturing a portion of the proteinaceous substance.

49. The method of claim 11, wherein denaturing the protein in situ in step (e) comprises denaturing all of the proteinaceous substance.

50. The method of claim 11, wherein denaturing the protein in situ in step (e) comprises denaturing a portion of the proteinaceous substance.

51. The biomolecular solder of claim 1, wherein the method of making the solder further comprises sterilizing the biomolecular solder before the step (d) placing of the pre-denatured solder in situ.

52. The biomolecular solder of claim 1, wherein the pre-denatured proteinaceous substance is shaped into a sheet, a tube, a partial tube, a strip, a patch, a hollow tube with a flanged end or a rod before the step (d) placing of the pre-denatured solder in situ, after the step (d) placing the pre-denatured solder in situ, or a combination thereof.

53. The method of claim 11, the desired shape comprises a sheet, a tube, a partial tube, a strip, a patch, a hollow tube with a flanged end or a rod before the step (d) placing of the pre-denatured solder in situ, after the step (d) placing the pre-denatured solder in situ, or a combination thereof.

54. A biomolecular solder comprising a protein comprising an albumin, an elastin, a collagen, a fibrinogen or a combination thereof, wherein the biomolecular solder is made by the method of claim 1, and the pre-denatured solder has been at least partially denatured while moist such that the protein bonds together and, when shaped, the shape of the solder is thereby essentially maintained and the solubility of the protein is reduced in a physiological fluid at body temperature.

55. The biomolecular solder of claim 54, wherein the solder is shaped before pre-denaturing.

56. The biomolecular solder of claim 54, wherein the solder is shaped after pre-denaturing.

57. The biomolecular solder of claim 54, wherein the protein comprises a bovine, rabbit, ovine, rat or horse serum albumin.

58. The biomolecular solder of claim 54, wherein the protein comprises a human albumin, a human elastin, a human fibrinogen, a human collagen or any combination thereof.

59. The biomolecular solder of claim 54, further comprising a dye for improving energy deposition into the solder when the solder is exposed to energy.

60. The biomolecular solder of claim 54, wherein the proteinaceous substance has been at least partially denatured while moist with a solvent.

61. The biomolecular solder of claim 60, wherein the solvent comprises an aqueous solvent.

62. The biomolecular solder of claim 61, wherein the aqueous solvent comprises water or saline.

63. A biomolecular solder made by a method comprising:
(a) providing a composition comprising a protein in a solvent;
(b) pre-denaturing the protein before placing the composition in situ by at least partially denaturing the protein while moist with the solvent such that at least a portion of the protein bonds together; and,
(c) shaping the pre-denatured protein, wherein the solder is shaped before, during or after the pre-denaturing of step (b), or a combination thereof.

64. The biomolecular solder of claim 63, further comprising steps
(d) placing the pre-denatured solder in situ, and
(e) further denaturing the protein in situ such that the final shape of the in situ-denatured solder is essentially maintained and the solubility of the protein is reduced in a physiological fluid at body temperature.

65. The biomolecular solder of claim 63, wherein the protein comprises albumin.

66. The biomolecular solder of claim 65, wherein the albumin comprises human albumin, bovine albumin, ovine albumin, horse albumin, rat albumin or a mixture thereof.

67. The biomolecular solder of claim 63, wherein the protein comprises collagen, elastin, fibrinogen or a combination thereof.

68. The biomolecular solder of claim 63, wherein pre-denaturing the protein before placing the composition in situ comprises the step of steam heating or immersion into hot water.

69. The biomolecular solder of claim 68, wherein the steam heating step comprises use of a temperature of between about 100° C. and 150° C.

70. The biomolecular solder of claim 63, wherein pre-denaturing the protein before placing the composition in situ comprises use of light, heat, radiation, ultrasound or chemicals.

71. The biomolecular solder of claim 63, wherein the step of denaturing the protein in situ comprises exposing the solder to light, heat, radiation, ultrasound or chemicals.

72. The biomolecular solder of claim 63, wherein the step of denaturing the protein in situ comprises exposing the solder to a laser energy.

73. The biomolecular solder of claim 72, wherein the laser energy that denatures the protein in situ comprises a power of about 90 mW and a wavelength of about 805 nm.

74. The biomolecular solder of claim 72, wherein the laser energy that denatures the protein in situ comprises a spot size at the solder of about 200 µm.

75. The biomolecular solder of claim 63, wherein further comprising a dye.

76. The biomolecular solder of claim 75, wherein the dye comprises an indocyanine green, a methylene blue or a fluorescein isothiocyanate.

77. The method of claim 24, wherein the biological tissue is a human or an animal tissue.

78. The method of claim 24, wherein a blood vessel, a nerve, a pancreatic duct, a liver vessel or duct, a cystic duct, a tear duct, prostatic duct, a ureter, urethra, an epididymis, a vas deferens, a fallopian tube, a bowel, a bronchi, a gastroenterological tube or duct, a respiratory tube or duct or a brain vessel, tube or duct are welded together.

79. A solder according to claim 1, wherein in step (b) the proteinaceous substance is fully denatured.

80. The biomolecular solder of claim 1 wherein the composition comprises a proteinaceous substance in a concentration in a range of between about 40% w/w and 80% w/w, or between about 45% w/w and 75% w/w, of the composition.

81. A biomolecular solder made by a method comprising
 (a) providing a composition comprising a proteinaceous substance in a solvent;
 (b) pre-denaturing the proteinaceous substance before placing the composition in situ by at least partially denaturing the proteinaceous substance while moist with the solvent such that at least a portion of the proteinaceous substance bonds together and the solubility of the proteinaceous substance is reduced in a physiological fluid at body temperature; and,
 (c) shaping the proteinaceous substance, wherein the solder is shaped before, during or after the denaturing of step (b), or a combination thereof, and, when shaped, the final shape of the solder is essentially maintained.

82. A sterile biomolecular solder made by a method comprising
 (a) providing a composition comprising a proteinaceous substance in a solvent;
 (b) pre-denaturing the proteinaceous substance ex vivo by at least partially denaturing the proteinaceous substance while moist with the solvent such that at least a portion of the proteinaceous substance bonds together; and,
 (c) sterilizing the pre-denatured solder.

83. A biomolecular solder composition comprising a shaped proteinaceous substance and a solvent, wherein the proteinaceous substance is at least partially denatured ex vivo while moist with the solvent such that at least a portion of the proteinaceous substance bonds together.

84. The composition of claim 83, wherein the proteinaceous substance is fully denatured.

85. The composition of claim 83, wherein the protein comprises an albumin, a collagen, an elastin, a fibrinogen, or any combination thereof.

86. A sterile shaped biomolecular solder comprising an at least partially cross-linked proteinaceous substance and a solvent, wherein the proteinaceous substance is at least partially cross-linked while moist with the solvent such that at least a portion of the proteinaceous substance bonds together.

87. A biomolecular solder comprising an at least partially cross-linked protein and a solvent, wherein the protein comprises an albumin, a collagen, an elastin, a fibrinogen, or any combination thereof, and is at least partially cross-linked while moist with the solvent.

88. A kit comprising the sterile biomolecular solder of claim 82.

89. A kit comprising the sterile shaped biomolecular solder of claim 86.

90. A kit comprising the biomolecular solder of claim 87.

91. A kit comprising the sterile biomolecular solder of claim 87, the sterile shaped biomolecular solder of claim 86 or the biomolecular solder of claim 87, and instructions for using the solder as set forth in claim 24.

* * * * *